United States Patent
Mostowy-Gallagher et al.

(10) Patent No.: US 12,385,079 B2
(45) Date of Patent: Aug. 12, 2025

(54) METHOD OF DETERMINING GLUCOSE CONCENTRATION

(71) Applicant: Sun Chemical Corporation, Parsippany, NJ (US)

(72) Inventors: Maura Mostowy-Gallagher, Carlstadt, NJ (US); Mohammad S. Farahat, Carlstadt, NJ (US); Russell Schwartz, Parsippany, NJ (US)

(73) Assignee: SUN CHEMICAL CORPORATION, Parsippany, NJ (US)

( * ) Notice: Subject to any disclaimer, the term of this patent is extended or adjusted under 35 U.S.C. 154(b) by 0 days.

(21) Appl. No.: 18/833,176

(22) PCT Filed: Mar. 10, 2023

(86) PCT No.: PCT/US2023/014944
§ 371 (c)(1),
(2) Date: Jul. 25, 2024

(87) PCT Pub. No.: WO2023/172715
PCT Pub. Date: Sep. 14, 2023

(65) Prior Publication Data
US 2025/0109423 A1    Apr. 3, 2025

Related U.S. Application Data

(60) Provisional application No. 63/318,857, filed on Mar. 11, 2022.

(51) Int. Cl.
| *C12Q 1/24* | (2006.01) |
| *C12Q 1/28* | (2006.01) |
| *C12Q 1/54* | (2006.01) |
| *G01N 21/78* | (2006.01) |

(52) U.S. Cl.
CPC    *C12Q 1/54* (2013.01); *C12Q 1/28* (2013.01)

(58) Field of Classification Search
None
See application file for complete search history.

(56) References Cited

U.S. PATENT DOCUMENTS

| 3,964,871 | A | 6/1976 | Hochstrasser |
| 4,340,669 | A | 7/1982 | Bauer |
| 4,427,770 | A | 1/1984 | Chen |
| 4,604,264 | A | 8/1986 | Rothe |
| 5,124,128 | A | 6/1992 | Hildenbrand |
| 5,183,742 | A | 2/1993 | Omoto |
| 5,378,638 | A | 1/1995 | Deeg |
| 6,444,169 | B1 | 9/2002 | Evtodienko |
| 7,533,630 | B2 | 5/2009 | Steckel |
| 8,062,902 | B2 | 11/2011 | Mestrallet |
| 10,660,301 | B1 | 5/2020 | Rotman |
| 2014/0230739 | A1 | 8/2014 | Goff |

FOREIGN PATENT DOCUMENTS

| CA | 1185153 A | 4/1985 |
| CA | 2019424 A1 | 1/1991 |
| DE | 3809523 A1 | 10/1989 |
| DE | 3922495 A1 | 1/1991 |
| DE | 4024544 A1 | 2/1992 |
| DE | 60219472 T2 | 1/2008 |
| EP | 0078971 B1 | 3/1985 |
| EP | 0113896 B2 | 11/1992 |
| EP | 0918881 A1 | 6/1999 |
| EP | 0918881 B1 * | 2/2004 |
| WO | WO 02/103353 A3 | 5/2003 |
| WO | WO2018/194964 A1 | 10/2018 |

OTHER PUBLICATIONS

International Preliminary Report on Patentability (Chapter II of the Patent Cooperation Treaty) issued in International Application No. PCT/US2023/014944, mailed Jun. 24, 2024.
International Search Report issued in International Application No. PCT/US2023/014944, mailed Jun. 16, 2023.
Written Opinion of the International Searching Authority issued in International Application No. PCT/US2023/014944, mailed Jun. 16, 2023.
Cha, Wang, He, and Ni (Development of cellulose paper testing strips for quick measurement of glucose using chromogen agent. Carbohydrate Polymers, May 2012 (DOI: 10.1016/j.carbpol.2012.02.028)).
Wilson, et al. (A low-cost inkjet-printed glucose test strip system for resource-poor settings. Journal of Diabetes Science and Technology, vol. 9(6):1275-1281, 2015).
Carrasco (Metal-organic frameworks for the development of biosensors: A current overview. Biosensors, 8:92, 2018).
Xu, et al. (Glucose oxidase-integrated metal-organic framework hybrids as biomimetic cascade nanozymes for ultrasensitive glucose biosensing, ACS Appl. Mater. Interfaces, 11: 22096-22101, 2019).
Biomass Pelletization: Standards and Production A. Garcia-Maraver and J. A. Perez Jimenez, Eds., WIT Press, Billerica, MA, 194 pages, Apr. 2015, ISBN: 978-1-78466-062-8.
Effect of Densification Conditions on Physical Properties of Pellets Made From Sawmill Residues American Journal of Engineering Research (AJER) e-ISSN: 2320-0847 p-ISSN : 2320-0936 vol. 5, Issue-6, 198-207 (2016).
Li Dejian et al: "A novel peroxidase mimetic Co-MOF enhanced luminol chemiluminescence and its application in glucose sensing", Sensors and Actuators B: Chemical, Elsevier BV, NL, vol. 296, May 31, 2019 (May 31, 2019), XP085739747, ISSN: 0925-4005, DOI: 10.1016/J.SNB.2019.126631 [retrieved on May 31, 2019].

* cited by examiner

*Primary Examiner* — Nghi V Nguyen
(74) *Attorney, Agent, or Firm* — Marian E. Fundytus; Amster Rothstein & Ebenstein LIP

(57) ABSTRACT

The present invention provides a powdered or fibrous or granular or pelleted material, and a method for preparing the material, for measuring glucose concentration in a liquid sample. The devices are typically in the form of a chemically treated granular or powdered or fibrous or pelleted material. The granular or powdered or pelleted or fibrous material is treated with a reagent mixture or solution comprising an enzyme or enzymes, or a combination of an enzyme with a pigment or another compound, a chromogen, and neutralizer. The chromogen in the reagent solution changes color when the reagent solution is exposed to glucose.

30 Claims, No Drawings

METHOD OF DETERMINING GLUCOSE CONCENTRATION

CROSS REFERENCE TO RELATED APPLICATIONS

The present application is a § 371 National Phase application based on PCT/US2023/014944 filed Mar. 10, 2023, which claims the benefit of U.S. Provisional Application No. 63/318,857, filed Mar. 11, 2022, the subject matter of each of which is incorporated by reference in their entirety.

FIELD OF THE INVENTION

The present invention is related to devices for testing the concentration of glucose in liquid samples. The devices of the present invention are in the form of an absorbent granular material, or microfiber, or powder, or pelleted material, treated with a reagent solution or mixture. The granular material or fiber or powder or pelleted material of the present invention is suitable to test glucose concentration in biological fluids, such as urine.

BACKGROUND OF THE INVENTION

Testing for glucose concentration in biological fluids, such as blood and urine, can aid in the diagnosis or monitoring of diseases, such as diabetes. One way to test the concentration of glucose in a liquid is to dip a test strip comprising reagents that react in the presence of glucose into the liquid to be tested. Most of the commercially available glucose test strips are prepared by impregnation of reagent solutions into absorbent substrates, such as filter paper. Others are extruded or blade coated with a complex structure. There remains a need for an indicating substrate that can be distributed over a large area in order to contact the liquid so that a bulk liquid sample does not have to be collected. For example, an indicating powder or granular material can be scattered across a litterbox where it is likely to be contacted with cat urine, where it can indicate the presence of glucose and an estimated concentration of glucose, or it can be blended with a cat litter.

U.S. Pat. No. 3,964,871 describes a device for testing glucose concentration in biological fluids which comprises a support-member impregnated with indicator reagent solutions. The preferred support-member is an absorbent material, which is then affixed to a hydrophobic second support member, such as a polymer film. A plurality of reagent impregnated absorbent support-members, each impregnated with a different reagent solution, are affixed to the second support member in discrete zones.

U.S. Pat. No. 4,340,669 provides a method to detect and differentiate between very high concentrations of glucose in biological fluids. The primary chromogen used in the reagent solutions is m-anisidine, which is toxic. Secondary chromogens are used to enable differentiating at very high concentrations of glucose, such as between 2,000 mg/dL and 5,000 mg/dL.

U.S. Pat. No. 4,427,770 discloses an analytical element produced by impregnating a carrier with a solution of 4-aminoantipyrine and a benzoic acid, a glucose oxidase, and peroxidase. A second solution of a semi-permeable polymer is then applied to the carrier.

EP 0078 971 (CA 1185153) describes a vehicle for glucose determination containing glucose oxidase, peroxidase, a chromogen, a nitrate, and, where appropriate, a UV-absorber. These agents are applied to the support matrix via impregnation.

DE 3809523 (U.S. Pat. No. 5,124,128) describes a process for the production of porous membranes, the membranes produced therewith, and their use as support matrices in test strips. The support with the membrane is immersed in the reagent solution. Under production conditions, impregnation can be done by means of an extrusion caster.

DE 4024544 (U.S. Pat. No. 5,378,638) describes a support layer containing a reagent applied in a defined pattern by means of an inkjet process. The pattern comprises several sets of compartments, with each set containing a different reagent. One set of compartments contains a reagent that is bound to the support layer. One or more other sets of compartments contain reagents that are soluble in the fluid to be tested, i.e. they are elutable. Upon application of the test fluid, the elutable reagents are dissolved in the test fluid, and carried to the bound reagent, whereby a reaction takes place if glucose is present.

DE 1984 5771 describes glucose test strips which contain a reactive composition of 4-6 wt % peroxidase, 2-3 wt % glucose oxidase, 18-19 wt % o-tolidine, 4-6 wt % polycarbonic acid, and 66-72 wt % polypeptide binder.

DE 6021 9472 (WO 02/103353) describes a dry chemical test system for detecting glucose in animal urine, particularly cats. The chemical test system comprises two indicators, 4-AAP/phenol and potassium iodide for the detection and quantification of different concentrations of glucose in urine. In addition, the chemical test system contains an inhibitor that reacts with the oxidized indicator until the inhibitor is saturated, thus providing a minimum threshold at which the presence of glucose will be indicated.

EP 0113896 (U.S. Pat. No. 4,604,264) describes test strips wherein the reagents are coated on a polymer fabric with a slotted nozzle or a rake. Between the reagent layer and the gripping film there is an additional absorbent layer. The various components are preferably held together by a transparent cover net.

DE 3922495 (CA 2019424) describes a multilayer system, wherein the chromogen is integrated in a polymer casting solution. This polymer solution and the GOD/POD/binder matrix are applied in separate layers to a perforated polyester fabric by the use of a blade. A double adhesive tape is used to stick the coated polyester film on a support polymer film, wherein a polymer net covers the upper side of the complex.

U.S. Pat. No. 5,183,742 describes a test device for detecting various substances, such as glucose, protein urobilinogen, and/or occult blood, in body fluids. The reagent solutions are solvent-based, wherein the reagents and other ingredients are dissolved in organic solvents. The reagent solutions can be applied to a substrate, such as a polystyrene film, by several methods, preferably silk-screen printing.

Cha, Wang, He, and Ni (Development of cellulose paper testing strips for quick measurement of glucose using chromogen agent. Carbohydrate Polymers, May 2012 (DOI: 10.1016/j.carbpol.2012.02.028)), describe cellulose paper-based glucose test strips comprising 2,4,6-tribromo-3-hydroxy benzoic acid (TBHBA) as the chromogen, glucose oxidase and peroxidase as the enzyme catalysts, and gelation as the enzyme stabilizer. The reagents are applied to the substrate by soaking the substrate in the reagent solution.

Wilson, et al. (A low-cost inkjet-printed glucose test strip system for resource-poor settings. Journal of Diabetes Science and Technology, Vol. 9(6):1275-1281, 2015) describe a low-cost inkjet printed glucose test strip system. Three of the ink cartridges in an inkjet printer are replaced with cartridges containing three different reagent solutions: a glucose oxidase solution, a peroxidase solution, and a chromogen solution. The reagent solutions are each printed in separate layers.

U.S. Pat. No. 6,444,169 B1 describes a device for glucose detection and quantification in urine comprised of two indicators, where the first indicator detects the presence of a low-to-medium concentration of glucose and a second indicates the presence of a higher concentration, and this chromogenic indicator mixture is impregnated onto a carrier. The first indicator prevents color development of the second chromogenic indicator unless the higher concentration of glucose is present.

U.S. Pat. No. 7,533,630 describes an animal litter composition impregnated with an agent to detect the presence of glucose and an odor control agent, an antistatic agent, a surfactant, and an anticlumping agent.

U.S. Pat. No. 8,062,902 describes a mammalian disease detection system comprised of clear or transparent particles such as silica gel that can visually reveal the presence of blood in urine, and which contain a pH indicator, a bilirubin detector, a protein detector, and a glucose detector.

U.S. Pat. No. 10,660,301 describes a litter containing chemical agents that change color in contact with urine or feces, where the color can indicate various medical diagnoses. The litter is a porous base where a first additive is contained within the pores and the second additive is applied to the exterior of the porous base.

Carrasco (Metal-organic frameworks for the development of biosensors: A current overview. Biosensors, 8:92, 2018) reviews the use of metal-organic frameworks (MOFs) in biosensors. The metal in an MOF can be iron (Fe), europium (Eu), chromium (Cr), copper (Cu), cobalt (Co), nickel (Ni), aluminum (Al), and zinc (Zn). MOFs can measure the concentration of hydrogen peroxide in a solution, and the sensing can be electrochemical, chemiluminescent, fluorescent, visible UV, or localized surface plasmon resonance. Lack of selectivity has been a problem for the development of new MOFs.

Xu, et al. (Glucose oxidase-integrated metal-organic framework hybrids as biomimetic cascade nanozymes for ultrasensitive glucose biosensing, ACS Appl. Mater. Interfaces, 11:22096-22101, 2019) describes the preparation and use of an integrated enzyme system, wherein glucose oxidase (GOx) is immobilized on an Fe-MOF via an amidation coupling reaction, with the assistance of crosslinking agents. The integrated enzyme system was more sensitive that a simple mixture of Fe-MOF and GOx.

None of the cited references refers to a powder, granule, pellet, or fiber containing an indicator material that can be distributed or scattered in a defined area (e.g. a cat litterbox) to indicate the presence of glucose and an estimated concentration of glucose in biological fluids, such as urine.

BRIEF SUMMARY OF THE INVENTION

The present invention provides simple devices for the determination of glucose in biological fluids. In a preferred embodiment, the devices are in the form of a cellulosic fiber or powder or granules which have been treated with a formulation containing reagents for the detection of glucose.

In a particular aspect, the present invention provides a substrate comprising a precipitated reagent solution or mixture for determining glucose concentration in a liquid sample, wherein the substrate is a powdered, granular, pelleted, or fibrous material, and wherein the reagent solution or mixture comprises:

(a) one or more oxidase enzymes;
(b) one or more of the following:
  i. one or more peroxidase enzymes; and/or
  ii. one or more non-enzyme based materials that are enzyme-stabilizing, and/or have some enzymatic or catalytic activity;
(c) one or more chromogens; and
(d) water.

In certain embodiments, the reagent solution or mixture is applied on the substrate via spraying the reagent solution or mixture onto the granules or powder or fibers or pellets, or by spraying the reagent solution onto the granular or fibrous or powder or pellet substrate with tumbling or mixing, or by immersion of the granules or powder or fibers or pellets in the reagent solution, or by spraying or scattering the granules or fibers or powder or pellets onto or into the liquid, or by spraying the liquid and the powder together.

In certain embodiments, an additional material may be used to provide stability to the enzyme or enzymes.

In certain embodiments, a material used to provide stability to a component enzyme may also have a secondary function as an indicator. For example, certain metal-organic frameworks (MOFs), such as Fe-MIL-88B-$NH_2$, with the chemical formula $Fe_3O(H_2N\text{-}BDC)_3$, where BDC is benzene dicarboxylate, can be used to immobilize glucose oxidase enzyme to create a hybrid particle dispersion (Fe-MOF-GOX) in water. In combination with certain chromogens this can detect glucose in solution in the same way by the reaction of the glucose with GOX to liberate hydrogen peroxide. In this embodiment, the iron oxide-based MOF has peroxidase like activity.

In certain embodiments, various amounts of the treated granules or powder or fibers or pellets may be distributed in a particular region, wherein the treated materials would come in contact with the liquid sample.

In certain embodiments, a buffer or buffers may be added to the reagent solution or mixture. In some embodiments, a neutralizer may be added to the reagent solution or mixture. In some embodiments, the reagent solution or mixture may contain one or more organic solvents, e.g. to dissolve the chromogen.

In one embodiment, the liquid sample is urine.

These and other objects, advantages, and features of the invention will become apparent to those persons skilled in the art upon reading the details of the formulations and methods as more fully described below.

DETAILED DESCRIPTION OF THE INVENTION

The present invention provides simple devices for the determination of glucose in biological fluids. The devices are simple to use and can be produced with maximum efficiency. The devices are provided in the form of granules, powder, pellets, or fibers. The test devices of the present invention are particularly suited to measuring glucose concentration in a urine sample.

The test devices are prepared by applying a reagent solution or mixture to a granular or powder or pellet or fibrous substrate. The reagent solution or mixture is preferably applied by either spraying, tumbling, agitation, soaking, immersion, sprinkling, scattering, or otherwise blending.

The reagent solution or mixture comprises one or more oxidases, one or more peroxidases or non-peroxidase-based material that can substitute for a peroxidase, such as an iron oxide-based metal organic framework (MOF), or a pigment, or other agent or compound, and one or more chromogens, and water and/or other solvents. The reagent solution or mixture may also comprise one or more neutralizers to create a certain threshold of detection, below which no color would be present. The reagent solution or mixture may also contain one or more buffers to maintain the pH within a desired range and improve the stability of the solution.

It is to be understood that the foregoing general description and the following detailed description are exemplary and explanatory only, and are not restrictive of any subject matter claimed.

Headings are used solely for organizational purposes, and are not intended to limit the invention in any way.

Unless otherwise defined, all technical and scientific terms used herein have the same meaning as is commonly understood by one of skill in the art to which the inventions belong. All patents, patent applications, published applications and publications, websites and other published materials referred to throughout the entire disclosure herein, unless noted otherwise, are incorporated by reference in their entirety for any purpose. Although any methods and materials similar or equivalent to those described herein can be used in the practice or testing of the present invention, the preferred methods are described.

Definitions

In this application, the use of the singular includes the plural unless specifically stated otherwise. As used herein, the singular forms "a," "an" and "the" are intended to include the plural forms as well, unless the context clearly indicates otherwise.

In this application, the use of "or" means "and/or" unless stated otherwise. Also, when it is clear from the context in which it is used, "and" may be interpreted as "or," such as in a list of alternatives where it is not possible for all to be true or present at once.

As used herein, the terms "comprises" and/or "comprising" specify the presence of the stated features, integers, steps, operations, elements, and/or components, but do not preclude the presence or addition of one or more other features, integers, steps, operations, elements, components, and/or groups thereof. Furthermore, to the extent that the terms "includes," "having," "has," "with," "composed," "comprised" or variants thereof are used in either the detailed description or the claims, such terms are intended to be inclusive in a manner similar to the term "comprising."

When the terms "consist of", "consists of" or "consisting of" is used in the body of a claim, the claim term set off with "consist of", "consists of" and/or "consisting of" is limited to the elements recited immediately following "consist of", "consists of" and/or "consisting of", and is closed to unrecited elements related to that particular claim term. The term 'combinations thereof', when included in the listing of the recited elements that follow "consist of", "consists of" and/or "consisting of" means a combination of only two or more of the elements recited.

As used herein, ranges and amounts can be expressed as "about" a particular value or range. "About" is intended to also include the exact amount. Hence "about 5 percent" means "about 5 percent" and also "5 percent." "About" means within typical experimental error for the application or purpose intended.

It is to be understood that wherein a numerical range is recited, it includes the end points, all values within that range, and all narrower ranges within that range, whether specifically recited or not.

Throughout this disclosure, all parts and percentages are by weight (wt % or mass % based on the total weight) and all temperatures are in ° C. unless otherwise indicated.

As used herein, the terms "reagent solution," "reagent mixture," and "reagent solution or mixture" refer to the prepared solution or mixture of enzymes, chromogens, and other suitable ingredients. It is understood that these terms are used interchangeably, and that the recitation of any of these terms, in combination or singly, includes all forms of mixtures, such as solutions, dispersions, or other types of mixtures.

As used herein, the term "chromogen" refers to a substance that can be converted to a dye or other colored compound when oxidized. In the present invention, the chromogens typically react with hydrogen peroxide, in a reaction catalyzed by a peroxidase, or another compound having peroxidase-like or catalytic activity, to form an oxidized colored compound.

As used herein, "unit" or "U" refers to enzyme activity. Enzyme unit, as understood by anyone skilled in the art, is defined as the amount of enzyme that catalyzes the conversion of a specified amount of substrate per minute under the specified conditions (usually temperature, pH, and substrate concentration) which are optimal for a given enzyme, depending on the supplier. For example, an enzyme unit for glucose oxidase may be defined as the amount of enzyme which oxidizes 1 micromole of glucose to gluconate and $H_2O_2$ (liberating one micromole of $H_2O_2$) at a temperature of about 25° C. to about 35° C., and at a pH of about 5 to about 7. The glucose oxidase and peroxidase used in the examples described herein were obtained from BBI Solutions. In the case of glucose oxidase, an enzyme unit is the amount of enzyme which causes the liberation of 1 micromole of $H_2O_2$ (from the oxidation of 1 micromole of glucose) per minute at 25° C. and pH 7.0. In the case of peroxidase, an enzyme unit is the amount of enzyme which catalyzes the production of one mg of purpurogallin (from the reaction of pyrogallol and hydrogen peroxide) in 20 seconds at 20° C. and pH 6.0.

Glucose Test Devices

The present invention provides simple devices for the determination of glucose in biological fluids. In a preferred embodiment, the present invention relates to the determination of glucose in urine, by applying a glucose-oxidase/peroxidase enzyme system (GOX/POD). The GOX/POD and other ingredients are dissolved or dispersed in a water-based solution, which is then added to an aqueous solution to prepare a reagent solution or mixture. The reagent solution contains one or more chromogens that will change color when glucose is present in the fluid sample. In another preferred embodiment, the peroxidase in the reagent solution is replaced with an enzyme stabilizing material, an enzyme stabilizing material that has enzymatic or catalytic activity, or a pigment that has enzymatic or catalytic activity. In a preferred embodiment, the peroxidase is replaced by a metal-organic framework. The reagent solution is sprayed or applied onto a substrate. Methods of application include, but are not limited to, spraying, tumbling, agitation, soaking, immersion, sprinkling, or otherwise blending.

The present invention provides a method to produce the powdered, granular, pelleted, or fibrous test devices, and the test devices resulting from the method.

A powder is defined as a collection of finely divided loose, solid particles or granules, or a dry bulk solid composed of fine particles that may flow freely when shaken or tilted. The terms powder and granular are sometimes used to distinguish between separate classes of materials. Generally, powders have finer grain sizes, typically in the range of microns or nanometers, and granules are coarser, and do not tend to form clumps except when wet. Powders may be considered a subclass of granular materials, in which the discreet particles tend to be smaller, and may clump together when wet. Generally, powders are based on particles in the size range of nanometers to microns. Granular materials can be comprised of particles into the millimeter size range. Both powders and granular materials are polydisperse, which means that they have a particle size distribution. The width of this distribution can affect the properties, such as the bulk density and flowability. Particle size distributions for granular and powdered materials can be measured using sieve methods, particularly in the range of 0.4-1.25+ mm. Sieve analysis makes use of a stack of test sieves with a range of nominal screen openings that can be agitated so that a sample material can pass through the sieves, and after testing the remaining material on each successive sieve is weighed and recorded. Alternatively, a qualitative particle size distribution for a given material can be measured using optical microscopy. A quantitative result can be obtained with the use of image processing software.

Granular or powdered materials may be comprised of compressed aggregates of smaller particles or fibers. An example is Gransorb, comprised of recycled paper fibers formed into particles ranging from 0.5 mm to 3 mm. The primary fibers themselves are about 20-40 microns in thickness, and millimeter scale in length. These and similar granular materials may also contain binders to create larger particles.

A fiber is a natural or artificial substance that is significantly longer than it is wide. Fibers can be defined as an elongated material having an approximately equiaxed and uniform transverse cross-section of diameter or thickness less than 250 microns, and an aspect ratio less than about 0.01, where the aspect ratio is defined as the ratio of fiber cross-sectional diameter (or thickness) to fiber length.

Pellets refer to small, rounded, sometimes cylindrical, particles of a solid substance, especially compressed materials. Pellets can have a higher density than the starting material due to this compression. For example, for some pelleted biomass materials, pelleting can increase the bulk density from 40-250 kg/m$^3$ to 600-800 kg/m$^3$ (BIOMASS PELLETIZATION: STANDARDS AND PRODUCTION A. Garcia-Maraver and J. A. Perez Jimenez, Eds., WIT Press, Billerica, MA, 194 pages, April 2015, ISBN: 978-1-78466-062-8).

As another example, sawdust can be compressed into pellets to be used as fuel or for other applications. Sawdust pellets can attain values between 0.856 kg/dm$^3$ and 1.093 kg/dm$^3$ for unit density, and 480.0 kg/m$^3$ and 603.0 kg/m$^3$ for bulk density (Effect of Densification Conditions on Physical Properties of Pellets Made From Sawmill Residues American Journal of Engineering Research (AJER) e-ISSN: 2320-0847 p-ISSN: 2320-0936 Volume-5, Issue-6, 198-207 (2016)).

Unit density is the mass per volume of a given particle, where the bulk density is a property of powders, granules, and other divided solids, and is defined as the mass of many particles divided by the volume they occupy.

In more general terms, the aspect ratio may apply to non-fibrous particles, as well as fibrous particles, and is defined as the ratio of the smallest diameter and the largest diameter orthogonal to it:

$$A_R = d_{min}/d_{max}$$

One type of cellulose fiber used in this application is comprised of 20-40-micron diameter fibers, with lengths ranging from 100-500 microns, and having an aspect ratio of about 0.04 to 0.4. A preferred particle size distribution of cellulose fiber powder is fibers with diameter range of 1-60 microns and a length range of 10-1,000 microns, but more preferably 10-40 micron diameter and 100-500 micron length.

The glass fibers used in one example were 5-10 microns in diameter and millimeter scale in length, with aspect ratio of less than 0.002.

One example may use blended non-exfoliated vermiculite and mica particles: 10-250 microns with aspect ratio of about 0.3 to 1.0. For non-exfoliated vermiculite or blends of non-exfoliated vermiculite with mica and other silicates, the preferred particle size distribution is 1-500 microns, and more preferably 10-250 microns with aspect ratio of about 0.3 to 1.0.

Sawdust is another granular material with particles in the range of less than 20 microns to greater than 2 mm. Aspect ratios of sawdust can vary outside this range, but a typical example would be particles with aspect ratios of about 0.2-0.5. For sawdust the preferred particle size distribution is from 1-5,000 microns, and most preferably in the range of 20 microns to 2 mm, and with aspect ratios of about 0.2 to 0.5.

Exfoliated vermiculite particles range from 2-15 mm. For exfoliated vermiculite a preferred particle size distribution would be 1-30 mm, and most preferably 2-15 mm.

Granular cellulose can have particle sizes in the range of 1 mm with an average aspect ratio close to 1.0, but various grades may be significantly larger or smaller or broadly polydisperse. For granular cellulose the preferred particle size distribution is from 0.1 mm-5 mm with an aspect ratio of about 0.5-1.0, and most preferably 0.5-2 mm with an aspect ratio of 0.8-1.0.

Pellets, such as some wood-based cat litters, are comprised of pelleted particles with dimensions in the tens of millimeters.

While most of the commercially available glucose test strips are made by impregnation of a reagent solution into the substrate, others are blade coated or extruded with a complex structure. The present invention comprises applying the ingredient mixture (i.e., reagent solution) onto a simple powder, granular, pelleted, or fibrous substrate, for easy production of test devices.

The method of the present invention is based on an enzyme or bi-enzyme system, coupled with one or more chromogens, to detect glucose in a fluid sample. The enzymes are one or more oxidases, preferably glucose oxidases, and/or one or more peroxidases. The glucose oxidase catalyzes the conversion of glucose to gluconate and hydrogen peroxide. The peroxidase then catalyzes the reaction between the hydrogen peroxide and the chromogen, producing a color change. In some embodiments, an enzyme stabilizing material can be included. The enzyme stabilizing material can be a coordination complex where an enzyme fits into a cavity, and, in some instances, the enzyme stabilizing material may have peroxidase-like activity itself.

In a particular aspect, the present invention provides a substrate comprising a precipitated reagent solution or mixture for determining glucose concentration in a liquid sample, wherein the substrate is a powdered, granular, pelleted, or fibrous material, and wherein the reagent solution or mixture comprises:
(a) one or more oxidase enzymes;
(b) one or more of the following:
   i. one or more peroxidase enzymes; and/or
   ii. one or more non-enzyme based materials that are enzyme-stabilizing, and/or have some enzymatic or catalytic activity;
(c) one or more chromogens; and
(d) water.

The oxidase is preferably glucose oxidase. Glucose oxidase catalyzes the reaction between glucose, oxygen and water to produce gluconate and hydrogen peroxide. The glucose oxidase is typically present in the liquid in an amount of about 2,500 U/dl to about 100,000 U/dl.

Suitable glucose oxidases include those derived from fungi and insects, including glucose oxidase, glucose-1-oxidase, and glucose-2-oxidase. Typically, glucose oxidase derived from fungi is used in various industries, including biological tests. Suitable fungal sources of glucose oxidase include, but are not limited to, *Penicillium notatum, Aspergillus niger, Penicillium Amagasaki, Penicillium purpurogenum* No. 778, *Phanerochaete chrysosporium, Aspergillus flavus, Pencillium* sp, *Fusarium* sp, *Aspergillus terreus*, and the like.

The present invention may comprise one or more peroxidases. Peroxidase catalyzes the reaction of the hydrogen peroxide produced by the reaction catalyzed by glucose oxidase, with one or more chromogens to produce a color change in the reagent solution. The peroxidase is typically present in an amount of about 500 U/dl to about 15,000 U/dl, where U/dl is enzyme units per deciliter.

Suitable peroxidases include those derived from plants, fungi, and bacteria. Suitable plant peroxidases include, but are not limited to, horseradish peroxidase, soybean peroxidase, turnip peroxidase, radish peroxidase, cabbage peroxidase, broccoli peroxidase, apple peroxidase, orange peroxidase, tobacco peroxidase, green pea peroxidase, pumpkin peroxidase, papaya peroxidase, banana peroxidase, combinations thereof, and the like. For example, horseradish peroxidase is typically used in a bi-enzyme test system for glucose. Suitable microbial sources of peroxidase (e.g. bacteria, cyanobacteria, fungi, actinomycetes, etc.) include those isolated from, but not restricted to, *Streptomyces thermoviolaceus, Bacillus subtilis, Pseudomonas* sp, *Citrobacter* sp, *Anabaena* sp, *Candida krusei, Coprinopsis cinerea, Phanerochaete chrysosporium, Streptomyces* sp, *Thermobifida fusca*, yeast, and the like.

In some embodiments, the reagent of the present invention may comprise one or more non-enzyme based materials. The non-enzyme based materials may be selected from enzyme stabilizing materials, enzyme stabilizing materials having enzymatic or catalytic activity, pigments having enzymatic or catalytic activity, and combinations thereof. These non-enzyme based materials may be enzyme stabilizing materials. One such enzyme stabilizing material is metal-organic frameworks (MOFs). MOFs are synthetic coordination polymer hybrid materials, and are comprised of metal ions or metal clusters, and an organic linker. In one embodiment, glucose oxidase is complexed with an iron based MOF (Fe-MOF) to obtain a Fe-MOF-GOX compound. Another example of a non-enzyme based material is a pigment, such as hematin, which may react with the hydrogen peroxide produced by the reaction of the oxidase with glucose. Hematin, derived from porphyrin, contains iron in the ferric state ($Fe^{3+}$), and is a dark bluish or brownish color. Hematin is an exogenous source of heme and is used medically to treat porphyria and other biological deficits of hemoglobin. Unlike heme, which is also an iron complexed with porphyrin and contains ferrous ion (Fe II), hematin contains ferric ion (Fe III) and a coordinating hydroxyl group. This hydroxyl group forms the linkage of hematin to the organic structure of proteins to comprise enzymes such as hemoglobin and horseradish peroxidase. In some instances, the non-enzyme based material may have peroxidase-like or catalytic activity. In some embodiments, the non-enzyme based material may be used instead of peroxidase. The preferred range of Fe-MOF-GOX on the final glucose indicator is 20 ppm to 1% on a w/w basis, with a preferred range being 50 ppm to 500 ppm, and most preferred being about 100 to 200 ppm. The concentration of Fe-MOF-GOX in the liquid solution used to treat the solid substrate could be any concentration that would allow an effective deposition on the substrate by spraying, immersion, or by any of the other application methods earlier mentioned. The range for hematin in the GOX-hematin formulation could be from 1 ppm to 1% of the final glucose indicator, with a preferred level being 25 to 600 ppm, and the most preferred level is 50 to 150 ppm on a w/w basis.

The present invention comprises one or more chromogens. The chromogen reacts with the hydrogen peroxide, in a reaction catalyzed by the peroxidase, or non-enzyme based material having peroxidase or catalytic activity, to form an oxidized chromogen, or an oxidative addition product, to effect a color change when the reagent solution is exposed to glucose in the fluid sample. One or more chromogens may be used, and each chromogen is typically present in an amount of about 200 mg/dl to about 750 mg/dl. If more than one chromogen is used, the total amount of chromogens will be the sum of the amounts of each. For example, if two chromogens are used, the total amount of chromogens can be about 400 mg/dl to about 15,000 mg/dl. In certain embodiments, each chromogen may be present in an amount of about 200 mg/dl to about 700 mg/dl.

Suitable chromogens include but are not limited to: 4-aminoantipyrine (4-AAP); antipyrine; tribromo hydroxybenzoic acid (TBHBA); o-tolidine; 4-hydroxybenzoic acid; phenol, 4-bromophenol; 4-chlorophenol; 3,3'5,5'-tetramethylbenzoic acid (TMB); 2,2'-azino-bis(3-ethylbenzothiazoline-6-sulfonic acid) (ABTS), or other sulfur containing chromogenic compounds; vanillic acid; phenolic acids; o-dianisidine; phenol-4-sulfonic acid; resorcinol; other chromogenic oxygen acceptors; combinations thereof; and the like.

The reagent solution of the present invention may comprise one or more neutralizers. The neutralizers react with the oxidized form of the chromogen below a threshold level of glucose (e.g. 30 mg/dl), to bring the chromogen back to reduced form. Below the threshold level, the reagent solution remains colorless. Once the threshold level of glucose is reached, and the neutralizer is saturated, the chromogen is present in oxidized form, and the reagent solution changes color. The neutralizer, when used, is typically present in an amount of about 250 mg/kg to 1000 mg/kg of finished product.

Suitable neutralizers include, but are not limited to, L-cysteine, mercaptans, thiosulfates, gallic acid, ascorbic acid, combinations thereof, and the like.

The enzymes, chromogens, and neutralizers are typically dissolved or dispersed in a solution or dispersion. The solution or dispersion typically has a solids content of 1 wt % to 10 wt %, based on the total weight of the solution or dispersion. The viscosity of the solution or dispersion is typically about 3 cps to about 10 cps, but could be as high as 500 cps.

As described, the present invention employs an enzyme system for detection of glucose in a fluid sample. In one possible scheme, the glucose oxidase catalyzes the conversion of glucose to gluconate and hydrogen peroxide. The peroxidase then catalyzes the reaction between the hydrogen peroxide and the chromogen, producing a color change.

In one embodiment, the reagent solution comprises the chromogens 2,4,6-TBHBA and 4-AAP, and the color change is from colorless to a rose/pink or red, depending on the glucose concentration in the test liquid.

fur-containing compounds, as well as many others, and combinations thereof. The concentration of a chosen MOF material in the reagent liquid might be about 20 ppm to 1% if the application method makes use of an equivalent weight of reagent liquid sprayed onto solid substrate. However, the liquid might be more (or less) concentrated, as long as the final level desired on the substrate can be achieved. For example, if a highly efficient spray process can be achieved, and it would be desirable to have less water to remove after the application of liquid to solid substrate, then a more concentrated solution might be used in proportion. If half the water is to be used, then the concentration of the reagent liquid might be doubled. In a preferred example, one kilogram of glucose indicator with a final concentration of 200 ppm of Fe-MOF-GOX w/w might be produced by spraying

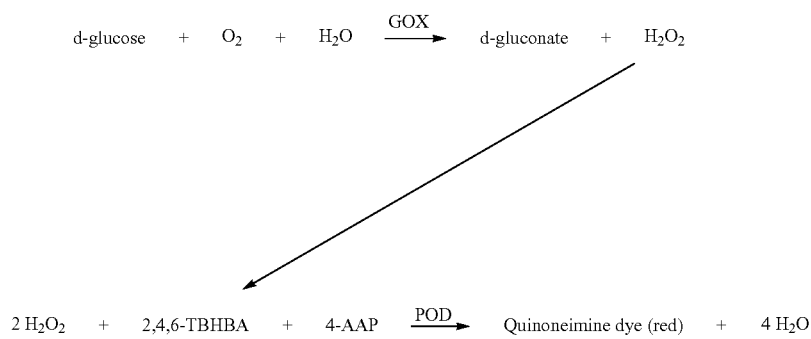

In another embodiment, the reagent solution comprises TMB as the chromogen, and the color change is from colorless to blue.

500 grams of a buffered reagent solution containing 400 ppm Fe-MOF-GOX onto 1 kg of substrate, and subsequently dried.

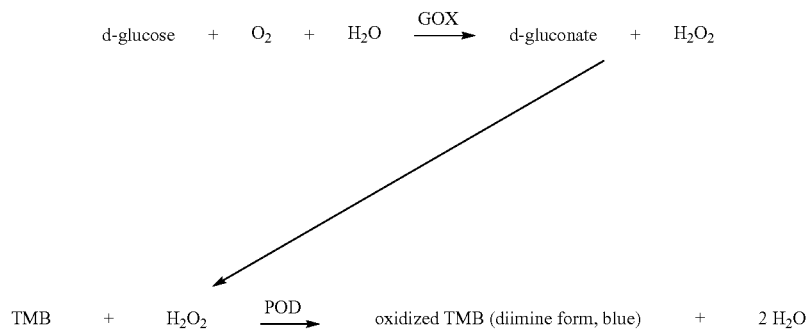

In another scheme, one or more of the enzymes can be stabilized by complexation within a metal-organic framework (MOF), to obtain a MOF-enzyme complex. MOFs are synthetic coordination polymer hybrid materials, and are comprised of metal ions or metal clusters, and an organic linker. MOFs are crystalline structures, having high surface areas. According to the IUPAC definition, MOFs are characterized by the presence of potential voids. Metals that are commonly used in MOFs are iron, copper, nickel, europium, chromium, cobalt, nickel, aluminum, zinc, and combinations thereof. Some examples of organic linkers used in MOFs include, but are not limited to, are carboxylic acids, nitrogen-containing compounds, porphyrins, metalloporphyrins, tetraphenylethylene, isophthalate, benzene compounds, sul- In a preferred embodiment, the MOF is iron-based (Fe-MOF), and is used to stabilize the GOX enzyme. In this scheme, the glucose oxidase part of Fe-MOF-GOX catalyzes the conversion of glucose to gluconate and hydrogen peroxide. The Fe-MOF part then catalyzes the reaction between the hydrogen peroxide and the chromogen, to produce an oxidized form of the chromogen, resulting in a color change. For example, glucose oxidase was reacted with a metal-organic-framework (MOF), Fe-MIL-88B-NH$_2$, using a well-known amidation reaction between the enzyme and the MOF, to link the GOX into the pore structure of the MOF. The MOF known as Fe-MIL-88B-NH$_2$ is comprised of iron oxide inorganic groups linked as a crystal structure with 2-aminoterephthalic acid ligands. A Fe-MOF-GOX is thus obtained. The Fe-MOF itself possesses peroxidase-like behavior, in that it can catalyze the oxidation of TMB chromogen by hydrogen peroxide, producing the colored oxidized version of TMB, or it can catalyze the oxidative addition of 4-aminoantipyrine and 2,4,6-tribromo-3-hydroxybenzoic acid, illustrated below. In some embodiments, the Fe-MOF replaces peroxidase.

Especially preferred is alpha cellulose fiber or granular cellulose. In some embodiments, the cellulosic substrate is preferably a powder or fiber or granular material with particle dimensions of equal to or greater than 20 μm, and with a bulk density of equal to or greater than 110 g/L. In some embodiments, the cellulosic substrate is a granular

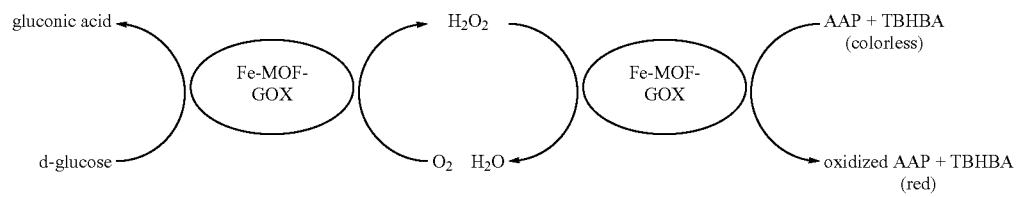

In other schemes, the peroxidase can be replaced by a pigment, such as hematin, that catalyzes the reaction between the hydrogen peroxide and the chromogen, to produce an oxidized form of the chromogen, resulting in a color change. Hematin ($C_{34}H_{34}FeN_4O_5$), derived from porphyrin, contains iron in the ferric state ($Fe^{3+}$), and is a dark bluish or brownish color. Hematin is an exogenous source of heme and is used medically to treat porphyria and other biological deficits of hemoglobin. Unlike heme, which is also an iron complexed with porphyrin and contains ferrous ion (Fe II), hematin contains ferric ion (Fe III) and a coordinating hydroxyl group. This hydroxyl group forms the linkage of hematin to the organic structure of proteins to comprise enzymes such as hemoglobin and horseradish peroxidase. The level of hematin used in the glucose indicator may be in the range of 1 ppm to 2% hematin on a w/w basin of the final material. A preferred level would be 25 ppm to 600 ppm, and most preferred is 50 to 200 ppm.

It would also be possible to incorporate small amounts of colorant into the reagent solutions, but this is typically not done as it may interfere with the perceived color change of the indicator.

A white pigment, such as titanium dioxide can be incorporated into the granular or fibrous or powdered substrate to intensify or modify the color change.

The reagent solution can be applied to the substrate by any suitable method. Preferred methods include spraying, spray-tumbling, mixing, immersion of powder, granular, pelleted, or fibrous substrate into the reagent solution, or agitation. It is to be understood that other methods of mixing or blending the solid substrate with the reagent solution could be used in the method of the present invention.

Typically, the substrate will be cellulose based, for example, cellulose microfiber, crystalline or amorphous, or recycled paper or paperboard-based materials, which could be powdered, fibrous, or granular. In a preferred embodiment an alpha-cellulose fiber is used. In another embodiment a cellulosic granular absorbent is used, such as Gran-Sorb. Other cellulosic materials used are for example, sawdust, paper, or ethyl cellulose. In other embodiments non-cellulosic substrates are used, such as, for example, Perlite, silica, silicate, sand, glass, clay, bentonite clay, wood-based, peat moss, quartz, mica, wax powders, augite, vermiculite, commercial cat litters, and inorganic pigments (e.g. titanium dioxide). In another embodiment a combination, blend, or mixture of powdered, fibrous, or granular substrates can be used.

material with a bulk density of about 500 g/L. Also preferred are silicate or vermiculite blends.

In a preferred embodiment, the reagent solution or mixture is applied to the substrate, and dried, to obtain a substrate comprising a precipitated reagent solution or mixture. Preferably, the oxidase is present in an amount of 7000 U per kg to 2,500,000 U per kg of finished dried glucose indicator substrate; the peroxidase, when included, is present in an amount of 2,000 U per kg to 700,000 U per kg of the finished dried glucose indicator substrate; the peroxidase alternative, when included, is used in the amount of 20 ppm to 1% MOF w/w relative to the finished dried glucose indicator substrate, or 1 ppm to 2% hematin w/w relative to the finished dried glucose indicator substrate; and the total amount of chromogens is 100 mg to 25 g per kg of finished dried glucose indicator substrate.

EXAMPLES

The present invention is further described by the following non-limiting examples, which further illustrate specific aspects of the invention, and are not intended to, nor should they be interpreted to, limit the scope of the invention in any respect.

Example 1. Reagent Solution 1 on Cellulose Powder

A reagent solution 1 for spraying onto cellulose powder was prepared according to the formula shown in Table 1.

TABLE 1

Formula of Reagent Solution 1

| Material | Amount |
| --- | --- |
| Glucose oxidase (GOX) | 23,600 U |
| Peroxidase (POD) | 6,900 U |
| 4-Aminoantipyrin (4-AAP) | 0.400 g |
| 2,4,6 Tribromo-3-hydroxyl benzoic acid (TBHBA) | 0.380 g |
| Gallic acid | 0.050 g |
| Water | 99.17 g |

This enzyme solution contains glucose oxidase as the primary enzyme to catalyze step one of the reaction described above, and a secondary enzyme, horseradish peroxidase, to catalyze the second step of the reaction, which is the oxidation by peroxide of the chromogens to produce the colored quinoneimine. The gallic acid is a neutralizing agent added to prevent color development in contact with glucose solutions below about 25 mg/dl. The viscosity was 5 cP at 23° C., as measured by a Brookfield LV rotational viscometer, model DV2T using the LV-01 (61) spindle, at 200 rpm. The viscosity was tested using the Brookfield LV rotational viscometer, model DV2T using the LV-01 (61) spindle, at 200 rpm, and 23° C., for all examples.

In Example 1, 100 g of the reagent solution of Table 1 was sprayed onto an equivalent weight of cellulose powder using a rotating open cylinder with interior baffles to facilitate mixing. After spraying the cellulose powder with the reagent solution with mixing to ensure a homogenous application, the powder was dried at ambient temperature in air to allow most of the water to evaporate. Some low level of residual moisture, less than 10% may be present on the cellulose. This residual moisture may be removed by ambient drying in a vacuum chamber, if desired. The final material contained 236 kU glucose oxidase and 69 kU peroxidase per kg cellulose powder. After drying, the powder was stored in a sealed container. An amount of this treated cellulose powder can be blended with cat litter and placed in a litter box or scattered on the surface of cat litter. After contact with aqueous glucose solutions, such as glucose in water, in synthetic urine, or in actual urine, a visual color change from colorless to pink to red occurred with the treated cellulose powder, where the color intensity increases with the level of glucose, as described in Table 2.

TABLE 2

Color change of Example 1 cellulose powder based on glucose concentration

COLOR CHANGE (starting color of cellulose powder → pink/red)

| | Glucose conc. | | | | |
|---|---|---|---|---|---|
| | 0 mg/dl | 25 mg/dl | 50 mg/dl | 100 mg/dl | 200 mg/dl |
| Color | None | Sl. Pink | Med. Red | Dark Red | Dark Red |

Table 2 indicates a colorless result for no glucose, and progressively darker color from pink to red with increasing glucose levels from 25 to 200 mg/dl.

Example 2. Reagent Solution 2 on Silica Gel Based Cat Litter

In Example 2, the reagent solution 2 described in Table 3 was spread into a shallow pan, and an additional quantity of a granular commercial cat litter based on silica gel was sprinkled over the solution, manually blended, and allowed to air dry at room temperature. The resulting treated silica gel contained 47 kU GOX and 12.8 kU POD per kg silica gel. After drying, the enzyme solution-treated cat litter was stored in a sealed container. After contact with glucose solutions, a visual color change from slight yellow to red occurred, where the color intensity increased with the level of glucose from 0 to 200 mg/dl, as summarized in Table 4.

TABLE 3

Formula of reagent solution 2

| Description | Amount |
|---|---|
| Glucose oxidase (GOX) | 6,672 U |
| Peroxidase (POD) | 1,850 U |
| Sodium dihydrogen phosphate monohydrate | 1.13 g |
| Disodium phosphate heptahydrate | 0.35 g |
| 4-Aminoantipyrine | 0.40 g |
| 2,4,6 Tribromo 3 Hydroxybenzoic acid | 0.38 g |

TABLE 3-continued

Formula of reagent solution 2

| Description | Amount |
|---|---|
| Gallic acid | 0.05 g |
| Water | 97.7 g |
| | 100.00 |

Reagent solution 2 contains a lower level of enzymes, and buffer salts to maintain the pH at 6.

TABLE 4

Color change of granular cat litter based on glucose concentration of Example 2
COLOR CHANGE (original color of cat litter → Sl. Yellow →red)

| | Glucose conc. | | | | |
|---|---|---|---|---|---|
| | 0 mg/dl | 25 mg/dl | 50 mg/dl | 100 mg/dl | 200 mg/dl |
| Color | Sl. Yellow* | Pink | Med Red | Dark Red | Dark Red |

(*original color of treated silica gel cat litter)

Table 4 indicates a slightly colored baseline result for no glucose, and progressively darker color from yellow to red with increasing glucose levels from 25 to 200 mg/dl when cat litter is used as the substrate.

Example 3. Blended Cat Litter and Cellulose Fiber Treated with Reagent Solution 3

In Example 3, a quantity of cellulose powder was treated with the reagent Solution 3 of Table 5 at four parts enzyme solution to three parts cellulose powder by weight and was allowed to dry at ambient temperature. The treated cellulose powder was then blended with the wood-based cat litter in the proportion of two parts treated cellulose powder to five parts cat litter by weight. The resulting blend of treated cellulose powder and wood based cat litter thus contained 91 kU GOX and 26 kU POD per kg of the cat litter-powder blend. After contact with glucose solutions, a visual color change from slight yellow to orange to red occurred, where the color intensity increased with the level of glucose, as summarized in Table 6.

TABLE 5

Formula of reagent solution 3

| Description | Amount |
|---|---|
| Glucose oxidase (GOX) | 24,000 U |
| Peroxidase (POD) | 6,938 U |
| Sodium dihydrogen phosphate monohydrate | 1.13 g |
| Disodium phosphate heptahydrate | 0.35 g |
| 4-Aminoantipyrine | 0.40 g |
| 2,4,6 Tribromo 3 Hydroxybenzoic acid | 0.38 g |
| Methylcellulose thickener, 400 cP | 1.50 g |
| Gallic acid | 0.05 g |
| Water | 96.19 g |
| | 100.00 |

Reagent solution 3 contains a lower level of enzymes, buffer salts to maintain the pH at 6, and a thickener which could be advantageous depending on the desired application process. The viscosity of this reagent solution was 34 cP at 23° C., as measured by a Brookfield LV rotational viscometer, model DV2T.

TABLE 6

Color change based on glucose concentration for example 3

| | COLOR CHANGE Sl. Yellow → Red Glucose conc. | | | |
|---|---|---|---|---|
| | 0 mg/dl | 50 mg/dl | 100 mg/dl | 600 mg/dl |
| Color | *Sl. yellow | Orange | Red | Dark red |

Table 6 indicates a slightly yellow colored baseline (*original color of cat litter) result for no glucose, and progressive color change from orange to red with increasing glucose levels from 50 to 600 mg/dl when cat litter blended with treated cellulose is used as the substrate.

Example 4. Granular Absorbent From Recycled Paper Treated With Enzyme Solution 3

In Example 4, an amount of commercially available granular absorbent based on recycled paper, such as GranSorb (which can be used as a cat litter), was first mixed with the enzyme solution 3 of Table 5 in the proportion of 1-part GranSorb to 1 part enzyme solution by weight. The treated GranSorb was allowed to dry at room temperature and was stored in a sealed container. The resulting treated GranSorb contained 240 kU GOX and 69 kU POD per kg of the finished material. After contact with glucose solutions a visual color change from *pink to dark red occurred, where the color intensity increased with the level of glucose, as summarized in Table 7.

TABLE 7

Color change of granular recycled paper absorbent based on glucose concentration of glucose solution

| | COLOR CHANGE pink + dark red | | | |
|---|---|---|---|---|
| Glucose conc. | 0 mg/dl | | 100 mg/dl | 250 mg/dl | 350 mg/dl |
| Color | *Sl Pink | | Red | Dark Red | Dark Red |

Example 5. Small Amounts of Enzyme-Treated Cellulose Powder Sprinkled Onto Cat Litter In Example 5, a small amount (0.10 grams) of enzyme solution-treated cellulose powder, such as that described in Example 1, was sprinkled on top of several pans containing several grams each of a commercial cat litter, such as Arm & Hammer Clump & Seal AbsorbX, to which was applied different concentrations of aqueous glucose solutions. After contact with glucose solutions, a visual color change from *off-white to red occurred, where the color intensity increased with the level of glucose, as summarized in Table 8. This example demonstrates the effectiveness of a very small amount of treated cellulose sprinkled on top of a bulk amount of cat litter.

TABLE 8

Color change based on concentration of glucose solution applied to treated cellulose powders scattered on cat litter

| | COLOR CHANGE colorless + pink - red | | | |
|---|---|---|---|---|
| Glucose conc. | 0 mg/dl | 50 mg/dl | 100 mg/dl | 250 mg/dl | 350 mg/dl |
| Color | *Off-white | Sl. Pink | Pink | Red | Red |

*Original color of treated cat litter

Table 8 shows the progression of color with increasing concentrations of glucose applied to treated cellulose powder scattered on top of AbsorbX cat litter.

Example 6. Enzyme-Treated Powder Blended in Bulk With a Commercial Cat Litter In Example 6, the enzyme-treated cellulose powder, such as that described in Example 1, was blended in with the bulk of cat litter using Arm & Hammer Clump & Seal Odor Blaster cat litter. In this case, blends were prepared using 0, 1, 5, and 10% w/w of enzyme treated cellulose powder, such as that of Example 1, blended with cat litter. In each case, 300 mg/dL glucose solution was added to determine if a color signal could be detected. The results in Table 9 show that as little as 1% blended enzyme treated powder can indicate elevated glucose levels.

TABLE 9

Color change based on weight percent of enzyme treated cellulose powder blended with cat litter and treated with 300 mg/dl glucose

| Percent enzyme-treated cellulose powder in blend with cat litter | 0% | 1% | 5% | 10% |
|---|---|---|---|---|
| Color | *Off-white | Small amount of visible red/pink specks (1-5%) | Significant amount of visible red/pink specks (10-40%) | Nearly all surface material is red/pink ($\geq$50%) |

*Original color of cat litter treated with Example 1 cellulose powder.

Table 9 shows that even a small amount (even as low as 1%) by weight of enzyme-treated cellulose powder (described in Example 1) blended with cat litter is sufficient to indicate elevated glucose levels in a 300 mg/dl solution of glucose applied to the cat litter. A blend of 1% treated cellulose mixed into commercial cat litter contains 2.4 kU GOX and 0.69 kU POD per kg of total cat litter mixture.

In Example 7, the reagent solution formula described in Table 10 was used to treat glass fibers, for example of the type used in non-woven GF/D fiber filters (Whatman Corp). The enzyme-treated glass fiber, 0.7 grams, was immersed in a shallow pan containing 4 grams of the reagent solution and allowed to dry at room temperature. The dried treated glass fiber was cut into strips, and each strip was contacted with a range of aqueous glucose solutions. The color change with concentration is summarized in Table 11.

TABLE 10

Formula of reagent solution 4

| Description | Amount |
|---|---|
| Glucose oxidase (GOX) | 13,330 U |
| Peroxidase (POD) | 3,544 U |
| Description | Amount |
| Sodium dihydrogen phosphate monohydrate | 1.13 g |
| Disodium phosphate heptahydrate | 0.35 g |
| 4-Aminoantipyrine | 0.40 g |
| 2,4,6 Tribromo 3 Hydroxybenzoic acid | 0.38 g |
| Gallic acid | 0.05g |
| Water | 97.69 g |
|  | 100.00 |

Reagent solution 4 contains a level of enzymes and includes buffers like that of reagent solution 2, but no thickener. The viscosity was 5 cP at 23° C., as measured by a Brookfield LV rotational viscometer, model DV2T.

TABLE 11

Color changed based on concentration of glucose solution applied to treated glass fibers COLOR CHANGE colorless + pink + red

| Glucose conc. | 0 mg/dl | 25 mg/dl | 50 mg/dl | 100 mg/dl | 150 mg/dl |
|---|---|---|---|---|---|
| Color | None | Pink | Red | Dark Red | Dark Red |

Table 11 shows the progression of color intensity with increasing glucose concentration of solutions applied to enzyme-treated glass fibers.

Example 8. Granular Absorbent Blended with $TiO_2$ and Treated with Reagent Solution 5

In Example 8, Reagent Solution 5, described in Table 13, was used to treat a blend of granular recycled paper absorbent blended with titanium dioxide rutile pigment. The blend was 17% titanium dioxide and 83% of the granular absorbent. The enzyme solution was added at 75% relative to the total mass of the absorbent and titanium blend, resulting in a finished material that contained 88.5 kU GOX and 25.9 kU POD per kg. The color change progression was pink rather than red, increasing in intensity with glucose concentration according to the results in Table 12. This blend increased the sensitivity range toward the determination of higher levels of glucose.

TABLE 12

Color change based on concentration of glucose solution applied to
treated blend of granular absorbent and titanium dioxide
COLOR CHANGE Colorless → Pink

| Glucose conc. | 0 mg/dl | 25 mg/dl | 50 mg/dl | 100 mg/dl | 500 mg/dl | 1000 mg/dl |
|---|---|---|---|---|---|---|
| Color | Colorless | Very Slight | Slight | Moderate | Strong | Strong |

Table 12 shows progressive color intensity with increasing glucose concentrations applied to a substrate comprised of granular absorbent from recycled paper blended with titanium dioxide white pigment and treated with enzyme solution.

Example 9. Blue Colored Glucose Indicator

In Example 9, the formula for Reagent Solution 5 as described in Table 13, was applied to an equivalent weight of cellulose fiber, allowed to dry at ambient temperature, and was then exposed to a range of glucose solutions of different concentrations from 0 to 500 mg/dl. The cellulose powder treated with this formulation showed a progressively darker blue color with increasing glucose concentrations as summarized in Table 14.

TABLE 13

Formula of reagent solution 5

| Description | Amount |
|---|---|
| Glucose oxidase (GOD) | 11,800 U |
| Peroxidase (POD) | 3,450 U |
| Sodium dihydrogen phosphate monohydrate | 1.07 g |
| Disodium phosphate heptahydrate | 0.33 g |
| 3,3',5,5'-tetramethylbenzene (TMB) | 0.42 g |
| Ethyl acetate | 4.64 g |
| Water | 93.54 g |
|  | 100.00 |

Reagent solution 5 contains TMB as the chromogen and ethyl acetate to solubilize the TMB separately before adding to the aqueous solution.

TABLE 14

Color change based on concentration of glucose solution applied
to enzyme treated cellulose fiber with TMB chromogen
COLOR CHANGE Colorless → Blue

| Glucose conc., mg/dl | 0 | 25 | 50 | 100 | 300 | 500 |
|---|---|---|---|---|---|---|
| Color | Colorless | Light Blue | Lt. Blue | Med. Blue | Dark Blue | Dark Blue |

Table 14 shows the progressive intensity of blue color with increasing glucose concentrations from 0 to 500 mg/dl.

Example 10. MOF-Stabilized GOX

In Example 10, glucose oxidase was reacted with a metal-organic-framework (MOF), Fe-MIL-88B-NH$_2$, using a well-known amidation reaction between the enzyme and the MOF. The MOF known as Fe-MIL-88B-NH$_2$ is comprised of iron oxide inorganic groups linked as a crystal structure with 2-aminoterephthalic acid ligands. The amidation reaction, well known in the art for covalently bonding proteins and peptides, was used to link the glucose oxidase into the pore structure of the MOF and is based on the reaction with 1-ethyl-3-(3-dimethylaminopropyl) carbodiimide (EDAC) and N-hydroxy succinimide (NHS). This reaction produced 400 nm Fe-MIL-88B-NH$_2$ (Fe-MOF) crystals with GOX covalently bound to the Fe-MOF crystals. In this example, the Fe-MOF-GOX was used in the absence of peroxidase enzyme to catalyze the oxidation of glucose to produce hydrogen peroxide according to the scheme described above. The Fe-MOF itself possesses peroxidase-like behavior, in that it can catalyze the oxidation of TMB chromogen by hydrogen peroxide, producing the colored oxidized diimine version of TMB, or it can catalyze the oxidative addition of 4-aminoantipyrine and 2,4,6-tribromo-3-hydroxybenzoic acid (see above).

The details of this procedure are described as follows in the embodiment of Example 10: The Fe-MOF crystals were first synthesized using a hydrothermal method. 1.66 mL of 0.4M FeCl3-6H$_2$O was added to a solution of 0.16 grams Pluronic F-127 non-ionic surfactant dissolved in 13.3 g deionized water and stirred for one hour. Next, 0.3 mL of 99.8% acetic acid and 0.06 g of 2-amino terephthalic acid was added and stirred for three hours. The solution was heated for 24 hours at 110° C. in an autoclave for the crystallization. The crystals were collected by centrifugation (30 minutes, 10,000 rpm), washed several times with ethanol, and redispersed in deionized water. The crystals were observed by Scanning Electron Microscopy (SEM) to be 400 nm in length. The SEM microscope was a Tescan Vega 3. The Fe-MOF crystals were reacted with GOX as follows: 6.0 mL of a solution (1,367 U/mL) of glucose oxidase (BBI Solutions, 268 U/mg) was stirred at 37° C. for 15 minutes with 300 microliters of 20 mM EDAC solution. To this was added 300 microliters of 20 mM NHS solution, 10 mL of Fe-MOF dispersion in water (3.5 mg/mL), and 20 mL of deionized water, and mixed for two hours at 36° F. The resulting particles were centrifuged, rinsed, and redispersed in 10 mL deionized water.

The Fe-MOF-GOX particles were dispersed in a solution of 17 mM 4-aminoantipyrine (AAP) and 11 mM 2,4,6-tetrabromohydroxybenzoic acid (TBHBA). The resulting dispersion contained 500 U/mL GOX enzyme. This dispersion was applied to an equivalent weight of cellulose powder and allowed to dry at ambient temperature.

The treated powder was then exposed to a range of glucose solutions of different concentrations from 0 to 150 mg/dl. The cellulose powder treated with this formulation showed a progressively stronger red color with increasing glucose concentrations as summarized in Table 15.

TABLE 15

Color change based on concentration of glucose solution applied to Fe-MOF-GOX treated cellulose fiber

| | COLOR CHANGE colorless - red | | | | |
|---|---|---|---|---|---|
| Glucose conc. | 0 mg/dl | 25 mg/dl | 50 mg/dl | 100 mg/dl | 150 mg/dl |
| Color | None | Pink | Red | Red | Dark Red |

The data in Table 15 show that when using Fe-MOF-GOX, the chromogen can be oxidized by the Fe-MOF part in the presence of $H_2O_2$, without the addition of a peroxidase.

Example 11. The Use of Hematin Pigment to Replace Peroxidase

In Example 11, ten grams of an aqueous solution of 102 ppm hematin dissolved in a pH 11 ammonia buffer solution was sprayed onto 20 grams of granular cellulose and allowed to dry. The ammonia was driven off to reduce the pH and allow the hematin to precipitate onto the cellulose substrate. Next, the reagent solution 6 of Table 16 was applied to an equivalent mass of the hematin treated cellulose powder, to give a final material containing 118 kU GOX per kg, and 51 ppm hematin in the finished material.

TABLE 16

| Formulation of reagent solution 6 | |
|---|---|
| Description | Amount |
| Glucose oxidase (GOX) | 11,800 U |
| Sodium dihydrogen phosphate monohydrate | 1.13 g |
| Disodium phosphate heptahydrate | 0.35 g |
| 4-Aminoantipyrine | 0.40 g |
| 2,4,6 Tribromo 3 Hydroxybenzoic acid | 0.38 g |
| Water | 97.76 g |
| | 100.00 |

Reagent solution 6 is a buffered solution containing glucose oxidase and no peroxidase.

The resulting material showed a progressively darker red color when glucose solutions were applied at concentrations from 0 to 200 mg/dl glucose, as described in Table 17.

TABLE 17

Color change based on concentration of glucose solution applied to GOX-hematin treated cellulose fiber

| | COLOR CHANGE colorless + red | | | | |
|---|---|---|---|---|---|
| Glucose conc. | 0 mg/dl | 25 mg/dl | 50 mg/dl | 100 mg/dl | 200 mg/dl |
| Color | None | Sl. Yellow | Pink | Red | Dark Red |

Example 12. The Use of Shredded Paper as Substrate

In Example 12, the glucose sensor substrate was shredded paper, which demonstrates the possibility of using recycled paper or pulp. The treated paper was prepared by adding a quantity of reagent solution 7, described in Table 18, to an equivalent weight of shredded paper and allowed to dry. The finished material contained 60 kU GOX and 23 kU peroxidase per kg.

TABLE 18

| Formulation of reagent solution 7 | |
|---|---|
| Description | Amount |
| Glucose oxidase (GOX) | 6,000 U |
| Peroxidase (POD) | 2,300 U |
| Sodium dihydrogen phosphate monohydrate | 1.13 g |
| Disodium phosphate heptahydrate | 0.35 g |
| 4-Aminoantipyrine | 0.40 g |
| 2,4,6 Tribromo 3 Hydroxybenzoic acid | 0.38 g |
| Gallic acid | 0.05 g |
| Water | 97.69 g |
| | 100.00 |

Reagent solution 7 is a buffered solution containing glucose oxidase and peroxidase.

The resulting material showed a progressively darker red color when glucose solutions were applied at concentrations ranging from 0 to 200 mg/dl glucose as described in Table 19.

TABLE 19

Color change based on concentration of glucose solution applied to enzyme-treated shredded paper COLOR CHANGE colorless → red

| Glucose conc. | 0 mg/dl | 25 mg/dl | 50 mg/dl | 100 mg/dl | 200 mg/dl |
|---|---|---|---|---|---|
| Color | None | Lt. Red | Red | Dark Red | Very Dark Red |

Example 13. Low Levels of Enzymes and Chromogens

In Example 13, low levels of enzymes and chromogens were used with shredded paper as the substrate to produce the glucose sensor. A quantity of reagent solution 8, as described in Table 20, was sprayed onto an equivalent weight of shredded paper and allowed to dry. The finished material contained 14 kU GOX and 3.6 kU peroxidase per kg.

TABLE 20

Formulation of reagent solution 8

| Description | Amount |
|---|---|
| Glucose oxidase (GOX) | 1,420 U |
| Peroxidase (POD) | 361 U |
| Sodium dihydrogen phosphate monohydrate | 0.27 g |
| Disodium phosphate heptahydrate | 0.08 g |
| 4-Aminoantipyrine | 0.10 g |
| 2,4,6 Tribromo 3 Hydroxybenzoic acid | 0.10 g |
| Gallic acid | 0.01 g |
| Water | 99.44 g |
|  | 100.00 |

Reagent Solution 8 is a buffered solution containing low levels of enzymes and chromogens.

TABLE 21

Color changed based on concentration of glucose solution applied to enzyme-treated shredded paper COLOR CHANGE colorless → red

| Glucose conc. | 0 mg/dl | 25 mg/dl | 50 mg/dl | 100 mg/dl | 600 mg/dl |
|---|---|---|---|---|---|
| Color | None | Red | Red | Red | Red |

The resulting material showed an intense red color when glucose solutions were applied at concentrations ranging from 25 to 600 mg/dl glucose, as described in Table 21.

Example 14. Low Levels of Enzymes and Chromogens, Concentrated Solution

In Example 14, less water was used to apply the enzyme solution to the cellulose. This would enable more efficient drying, requiring less water removal. In addition, low levels of enzymes and chromogens were used with granular cellulose as the substrate to produce the glucose sensor. A total of 24.7 grams of Reagent Solution 9 as described in Table 22, was sprayed onto 100 grams of granular cellulose and allowed to dry. The finished material contained 14.5 kU GOX and 4.3 kU peroxidase per kg. The total amount of chromogen was 0.38% w/w on the finished material.

TABLE 22

Formulation of Reagent Solution 9

| Description | Amount |
|---|---|
| Glucose oxidase (GOX) | 2,940 U |
| Peroxidase (POD) | 880 U |
| Sodium dihydrogen phosphate monohydrate | 1.13 g |
| Disodium phosphate heptahydrate | 0.35 g |
| 4-Aminoantipyrine | 0.40 g |
| 2,4,6 Tribromo 3 Hydroxybenzoic acid | 0.38 g |
| Gallic acid | 0.05 g |
| Water | 47.69 g |
|  | 50.00 |

Reagent Solution 9 is a concentrated buffered solution with lower levels of enzymes.

The resulting material showed a progressive color change when glucose solutions were applied at concentrations ranging from 0 to 200 mg/dl glucose as described in Table 23.

TABLE 23

Color change based on concentration of glucose solution applied to enzyme-treated granular cellulose COLOR CHANGE colorless + red

| Glucose conc. | 0 mg/dl | 25 mg/dl | 50 mg/dl | 100 mg/dl | 200 mg/dl |
|---|---|---|---|---|---|
| Color | None | Sl. orange | Orange | Red | Dark red |

The present invention has been described in detail, including the preferred embodiments thereof. However, it will be appreciated that those skilled in the art, upon consideration of the present disclosure, may make modifications and/or improvements on this invention that fall within the scope and spirit of the invention.

What is claimed:

1. A finished dried glucose indicator substrate, wherein the finished dried glucose indicator substrate comprises: a substrate comprising a precipitated reagent solution or mixture for determining glucose concentration in a liquid sample, wherein the substrate is a powdered, granular, pelleted, or fibrous material, and wherein the reagent solution or mixture comprises:
   (a) one or more glucose oxidase enzymes;
   (b) one or more of the following:
      i. one or more peroxidase enzymes; and/or
      ii. one or more non-enzyme based materials that are enzyme-stabilizing, and/or have some enzymatic or catalytic activity;
   (c) one or more chromogens; and
   (d) water;
   wherein, after application to the substrate, the reagent solution or mixture is dried on the substrate to remove the water, forming a dry, precipitated reagent mixture on the substrate, to provide a finished dried glucose indicator substrate;
   wherein the glucose oxidase is present in an amount of 7000 U per kg to 2,500,000 U per kg of finished dried glucose indicator substrate; the peroxidase, when included, is present in an amount of 2,000 U per kg to 700,000 U per kg of the finished dried glucose indicator substrate; the non-enzyme based materials that are enzyme-stabilizing, and/or have some enzymatic or catalytic activity, when included, is used in the amount of 1 ppm to 2% w/w relative to the finished dried glucose indicator substrate; and the total amount of chromogens is 100 mg to 25 g per kg of finished dried glucose indicator substrate.

2. The substrate of claim 1, wherein the powdered, granular, pelleted, or fibrous material is selected from the group consisting of cellulosic, vermiculite, quartz, mica, silicate, sand, glass, wood-based, clay, bentonite clay, inorganic pigment, and blends thereof.

3. The substrate of claim 1, wherein the non-enzyme based materials of the reagent solution or mixture are each independently selected from the group consisting of enzyme stabilizing materials, enzyme stabilizing materials having enzymatic or catalytic activity, pigments having enzymatic or catalytic activity, and combinations thereof.

4. The substrate of claim 3, wherein the non-enzyme based materials of the reagent solution or mixture comprise a metal-organic framework enzyme stabilizing material.

5. The substrate of claim 4, wherein the metal-organic framework exhibits enzymatic or catalytic activity.

6. The substrate of claim 4, wherein the metal of the metal-organic framework of the reagent solution or mixture is one or more selected from iron, copper, nickel, europium, chromium, cobalt, nickel, aluminum, zinc, and combinations thereof.

7. The substrate of claim 1, wherein the non-enzyme based material comprises iron oxide.

8. The substrate of claim 1, wherein the non-enzyme based materials of the reagent solution or mixture are selected from a metal-organic framework or hematin; wherein, when used, the metal-organic framework is present in an amount of 20 ppm to 1% metal-organic framework w/w relative to the finished dried glucose indicator substrate; and wherein, when used, the hematin is present in an amount of 1 ppm to 2% hematin w/w relative to the finished dried glucose indicator substrate.

9. The substrate of claim 1, wherein non-enzyme based materials of the reagent solution or mixture comprise a metal-organic framework, wherein the metal-organic framework of the reagent solution or mixture comprises iron.

10. The substrate of claim 8, wherein the metal-organic framework of the reagent solution or mixture comprises Fe-MIL-88B-$NH_2$, having the chemical formula $Fe_3O(H_2N\text{-}BDC)_3$, where BDC is benzene dicarboxylate.

11. The substrate of claim 1, wherein the substrate changes color upon exposure to glucose.

12. The substrate of claim 1, wherein at least one of the peroxidase enzymes of the reagent solution or mixture, when peroxidase is present, is horseradish peroxidase.

13. The substrate of claim 1, wherein the one or more chromogens of the reagent solution or mixture are selected from the group consisting of tribromo hydroxybenzoic acid (TBHBA), 4-aminoantipyrine (4-AAP), antipyrine, o-tolidine, 4-hydroxybenzoic acid, 4-chlorophenol, resorcinol, 3,3',5,5'-tetramethylbenzoic acid (TMB), vanillic acid, phenol, phenolic acids, o-dianisidine, phenol-4-sulfonic acid, 2,2'-azino-bis(3-ethylbenzothiazoline-6-sulfonic acid) (ABTS), other chromogenic oxygen acceptors, and combinations thereof.

14. The substrate of claim 1, wherein at least one of the chromogens of the reagent solution or mixture is tribromo hydroxybenzoic acid or 4-aminoantipyrine, or a combination thereof.

15. The substrate of claim 1, wherein a single chromogen is present in the reagent solution or mixture.

16. The substrate of claim 1, wherein the reagent solution or mixture further comprises one or more neutralizers; and/or wherein the reagent solution or mixture further comprises one or more solvents.

17. The substrate of claim 16, wherein the one or more neutralizers of the reagent solution or mixture are selected from the group consisting of L-cysteine, mercaptans, thiosulfates, gallic acid, ascorbic acid, and combinations thereof.

18. A method of preparing the powder, granular, pelleted, or fibrous finished dried glucose indicator substrate for determining glucose concentration in a liquid sample according to claim 1, comprising the steps of:
(a) providing a powdered, granular, pelleted, or fibrous substrate; and
(b) applying a reagent solution or mixture to the substrate, wherein the reagent solution or mixture comprises:
   i. one or more oxidase enzymes;
   ii. one or more of the following:
      (1) one or more peroxidase enzymes; and/or
      (2) one or more non-enzyme based materials that are enzyme-stabilizing, and/or have some enzymatic or catalytic activity;
   iii. one or more chromogens; and
   iv. water; and
(c) drying the reagent solution or mixture on the substrate, and thereby obtaining a substrate comprising a precipitated reagent solution or mixture wherein the oxidase is present in an amount of 7000 U per kg to 2,500,000 U per kg of finished dried glucose indicator substrate; the peroxidase, when included, is present in an amount of 2,000 U per kg to 700,000 U per kg of the finished dried glucose indicator substrate; the non-enzyme based materials that are enzyme-stabilizing, and/or have some enzymatic or catalytic activity, when included, is used in the amount of 1 ppm to 2% w/w relative to the finished dried glucose indicator substrate; and the total amount of chromogens is 100 mg to 25 g per kg of finished dried glucose indicator substrate.

19. The method of claim 18, wherein the reagent solution or mixture is applied to the substrate by spraying, immersing, mixing, blending, or tumbling.

20. The method of claim 18, wherein the substrate is cellulosic, vermiculite, quartz, mica, silicate, sand, glass, wood-based, clay, bentonite clay, or inorganic pigment, either singly, or in combinations thereof.

21. The method of claim 20, wherein the cellulosic substrate is a cellulosic powder or fiber or granular material with particle dimensions of equal to or greater than 20 μm, and with a bulk density of equal to or greater than 110 g/L.

22. The method of claim 20, wherein the cellulosic substrate is a granular material with a bulk density of 500 g/L.

23. The method of claim 18, wherein the substrate is wood based granular recycled material or wood cellulose based.

24. The method of claim 18, wherein the substrate is vermiculite.

25. The method of claim 18, wherein the substrate is a blend comprising vermiculite, and/or quartz, and/or mica; or wherein the substrate is a blend comprising a silicate, or sand, or glass fibers.

26. The method claim 18, comprising the additional step of blending the substrate with another material, or applying the substrate on top of another material.

27. The method of claim 26, wherein the substrate is blended with or applied on top of cat litter.

28. A test item or test material suitable to test glucose concentration in a liquid sample, comprising the substrate of claim 1.

29. The test item or test material of claim 28, wherein the test item is suitable to test glucose concentration in a liquid sample of urine.

30. The test item or test material of claim 28, wherein the test item or test material is cat litter.

* * * * *